US00PP11776P2

(12) United States Plant Patent
Zary

(10) Patent No.: US PP11,776 P2
(45) Date of Patent: Feb. 13, 2001

(54) HYBRID TEA ROSE PLANT NAMED 'JACKISCA'

(75) Inventor: Keith W. Zary, Thousand Oaks, CA (US)

(73) Assignee: Jackson & Perkins Wholesale, Inc., Medford, OR (US)

( * ) Notice: Under 35 U.S.C. 154(b), the term of this patent shall be extended for 0 days.

(21) Appl. No.: 09/234,787

(22) Filed: Jan. 20, 1999

(51) Int. Cl.[7] ..... A01H 5/00
(52) U.S. Cl. ..... Plt./140
(58) Field of Search ..... Plt./139, 140

(56) References Cited

PUBLICATIONS

UPOV–ROM, 1999/02, Plant Variety Database, GTI JOUVE Retrieval Software, citation for 'JACkisca'.*

* cited by examiner

*Primary Examiner*—Howard J. Locker
(74) *Attorney, Agent, or Firm*—Klarquist Sparkman Campbell Leigh & Whinston, LLP

(57) ABSTRACT

Hybrid tea rose plant having high production of red flowers on medium long stems having a long vase life; vigorous, upright growth; and resistance to powdery mildew.

1 Drawing Sheet

The present invention relates to a new and distinct variety of rose plant of the hybrid tea rose class which was originated by me by crossing the variety 'KORokis', unpatented, with the variety 'AROresas', U.S. Plant Pat. No. 6,670.

The primary objective of this breeding was to produce a new rose variety having a vigorous, upright growth habit; high production of medium length stems for cut flower production; long vase life; a flower color between the coral pink of the female parent and the red flower color of the male parent; and good resistance to powdery mildew. The objective was substantially achieved, along with other desirable improvements, as evidenced by the following unique combination of characteristics that are outstanding in the new variety and that distinguish it from its parents, as well as from all other varieties of which I am aware:

1. Long vase life;
2. High cut flower production;
3. Novel flower color;
4. Resistance to powdery mildew;
5. Vigorous, upright growth, and;
6. Medium, long stems.

'JACkisca' is a productive, hybrid tea rose with a vase life greater than fourteen days. 'JACkisca', under conventional greenhouse production (60° F. nights, 80° F. days) in Southern California will produce 180 stems/$m^2$ with stems averaging 22–24" long.

Asexual reproduction of this new variety by budding on Manetti rootstalk, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'KORokis' (unpatented).

*Pollen parent.*—'AROresas' (U.S. Plant Pat. No. 6,670).

Classification:

*Botanical.*—*Rosa hybrida.*

*Commercial.*—Hybrid Tea.

FLOWER

Observations made from specimens grown in a greenhouse environment at Somis, Calif., June 1997 to December 1998.

Blooming habit: Continuous.

Bud:

*Size.*—One and one-half inches long when the petals start to unfurl.

*Form.*—The bud form is long, pointed ovoid.

*Color.*—When sepals first divide, bud color is Red-Purple Group 60A. When half blown, the upper sides of the petals are close to Red Group 53B and the lower sides of the petals are close to Red Group 53D with distinctive veins showing.

*Sepals.*—Color: Green Group 138B with often a light blush in the center of the sepal of Greyed-Purple Group 184D. Surface texture: Covered in fine hairs. There are three normally appendaged sepals. There are two unappendaged sepals with hairy edges. Sepals are unusually long, up to one and one-half inches for appendaged sepals.

*Receptacle.*—Color: Yellow-Green Group 146C. Shape: Funnel. Size: Medium, about 7/16"×9/16". Surface: Smooth.

*Peduncle.*—Length: Medium, averaging about three to four inches. Surface: Smooth, with just an occasional gland. Color: Yellow-Green Group 146B with some Greyed-Purple Group 183D in bright sun. Strength: Stiff, erect.

Bloom:

*Size.*—Large. Average open size is four inches.

*Borne.*—Singly.

*Stems.*—Strength: Strong. Average length is about twenty-two to twenty-four inches.

*Form.*—When first open: High-centered. Permanence: All petals curl with some quilling.

*Petalage.*—Number of petals under normal conditions: 40–45.

*Color.*—The upper sides of the petals are Red Group 53B. The reverse sides of the petals are Red Group 53D with veins showing. The base of each petal has a quite large (5/16"×3/8"), White Group 155C color spot that at the point of attachment is Green-Yellow Group 1D. The major color on the upper side is Red Group 53B.

*Variegations.*—Occasional white streaks on the guard petals and sometimes a white streak on the upper surface of interior petals.

*Discoloration.*—The general tonality at the end of the first day: No change. At the end of the third day: No change. By day ten, in the vase, color fades to Red Group 53D.

*Fragrance.*—None.

Petals:

*Texture.*—Thick.

*Shape.*—Round.

*Form.*—Tips slightly recurved, edges slightly quilled.

*Arrangement.*—Imbricated. Petaloids in the center: None.

*Persistence.*—Petals drop off cleanly before drying.

*Lastingness.*—On the plant: Very Long (eight to nine days). As a cut flower: Very Long (about fourteen to sixteen days).

Reproductive parts:

*Anthers.*—Size: Medium. Quantity: Many. Color: Yellow-Orange Group 20B. Arrangement: Regular around styles.

*Filaments.*—Color: White Group 155D, sometimes with a very light pink blush.

*Pollen.*—Color: Yellow-Orange Group 20C.

*Styles.*—Color: Yellow-Green Group 145C.

*Stigmas.*—Color: Yellow-White Group 158C.

Plant:

*Form.*—Bush.

*Growth.*—Vigorous. Mature plant height is about six feet, width is about 3½ feet., after one year's growth in a greenhouse.

Foliage: Number of leaflets on normal mid-stem leaves: Five or seven.

*Size.*—Medium (5" long×3½" wide).

*Quantity.*—Abundant.

*Color.*—New foliage: Upper surface: Greyed-Red Group 178A. Lower surface: Greyed-Red Group 178A. Old foliage: Upper surface: Green Group 137A. Lower surface: Green Group 138B.

Leaflets:

*Shape.*—Pointed oval.

*Texture.*—Leathery.

*Edge.*—Serrated.

*Serration.*—Single, small.

*Petiole rachis.*—Color: Green Group 146C. The upper surface of the rachis often, especially on newly mature leaves, has a purplish caste close to Red-Purple Group 59A.

*Petiole underside.*—Rough with prickles and glands.

*Stipules.*—Short (3/8"–7/16"), serrated, bearded.

*Disease resistance.*—Resistant to mildew under normal growing conditions. Not tested for blackspot and rust.

Wood:

*New wood.*—Color: Greyed-Red Group 178B. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Short, straight to hooked slightly downward.

*Color when young.*—Greyed-Orange Group 178B.

*Color when mature.*—Greyed-Orange Group 173D.

Small prickles:

*Quantity.*—On main stalks: None. On laterals: None.

I claim:

1. A new and distinct variety of rose plant of the hybrid tea class, substantially as herein shown and described, characterized particularly by its high production of red flowers on medium long stems having a long vase life; its vigorous, upright growth; and resistance to powdery mildew.

* * * * *

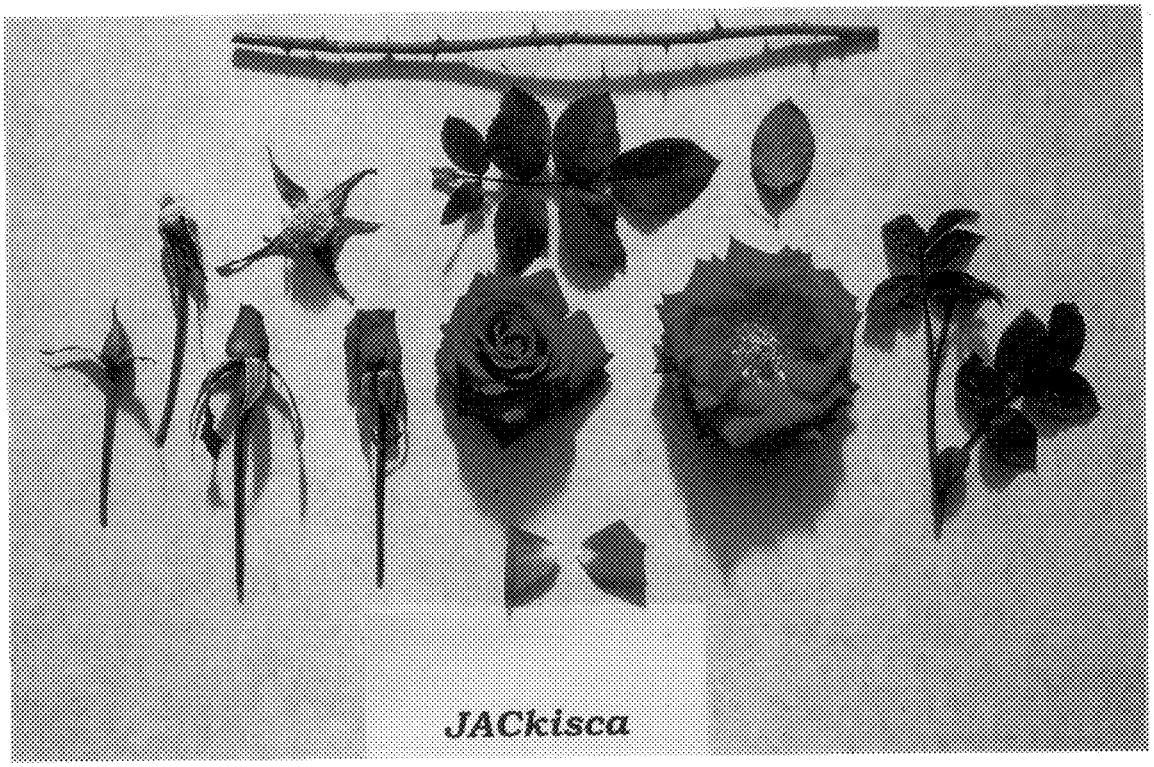
JACkisca